United States Patent
Leitner et al.

(10) Patent No.: US 6,877,239 B2
(45) Date of Patent: Apr. 12, 2005

(54) METHOD AND DEVICE FOR CHECKING A MARKING ELEMENT FOR DISPLACEMENT

(75) Inventors: Francois Leitner, Uriage (FR); Benoit Mollard, Echirolles (FR)

(73) Assignee: AESCULAP AG & Co. KG, Tuttlingen (DE)

( * ) Notice: Subject to any disclaimer, the term of this patent is extended or adjusted under 35 U.S.C. 154(b) by 0 days.

(21) Appl. No.: 10/244,000

(22) Filed: Sep. 13, 2002

(65) Prior Publication Data

US 2003/0056385 A1 Mar. 27, 2003

(30) Foreign Application Priority Data

Sep. 15, 2001 (DE) .......................................... 101 45 587

(51) Int. Cl.$^7$ ............................................... A61B 5/103
(52) U.S. Cl. ............................ 33/512; 33/511; 606/130
(58) Field of Search .......................... 33/511, 512, 1 N, 33/1 PT, 534, 700; 606/72, 73, 130

(56) References Cited

U.S. PATENT DOCUMENTS

| | | | |
|---|---|---|---|
| 4,576,158 A | * | 3/1986 | Boland ........................ 606/102 |
| 4,646,752 A | * | 3/1987 | Swann et al. ................. 33/512 |
| 4,986,280 A | * | 1/1991 | Marcus et al. ................ 33/512 |
| 4,991,579 A | | 2/1991 | Allen |
| 5,249,581 A | * | 10/1993 | Horbal et al. ................ 600/407 |
| 5,291,901 A | * | 3/1994 | Graf ............................. 33/512 |
| 5,493,788 A | * | 2/1996 | Richardson .................. 33/512 |
| 5,807,252 A | | 9/1998 | Hassfeld et al. |
| 6,074,394 A | * | 6/2000 | Krause ......................... 606/86 |
| 6,241,735 B1 | | 6/2001 | Marmulla |
| 2002/0147416 A1 | * | 10/2002 | Zogbi et al. .................. 33/512 |

FOREIGN PATENT DOCUMENTS

| | | |
|---|---|---|
| DE | 38 38 011 | 7/1989 |
| DE | 195 06 197 | 9/1996 |
| DE | 694 24 416 | 5/2000 |
| EP | 0 705 074 | 5/2000 |
| WO | 99/21498 | 5/1999 |

* cited by examiner

Primary Examiner—Christopher W. Fulton
Assistant Examiner—Madeline Gonzalez
(74) Attorney, Agent, or Firm—Barry R. Lipsitz; Douglas M. McAllister

(57) ABSTRACT

To make available a method for checking a marking element for displacement in relation to a holding structure, in particular a bone, on which this marking element is fixed, said marking element being used for determining position in navigational surgery, and said marking element functioning with the greatest possible precision, it is proposed to choose a point of orientation which is in a unique relationship to the holding structure and to monitor the position of the point of orientation in a reference system of the marking element.

22 Claims, 2 Drawing Sheets

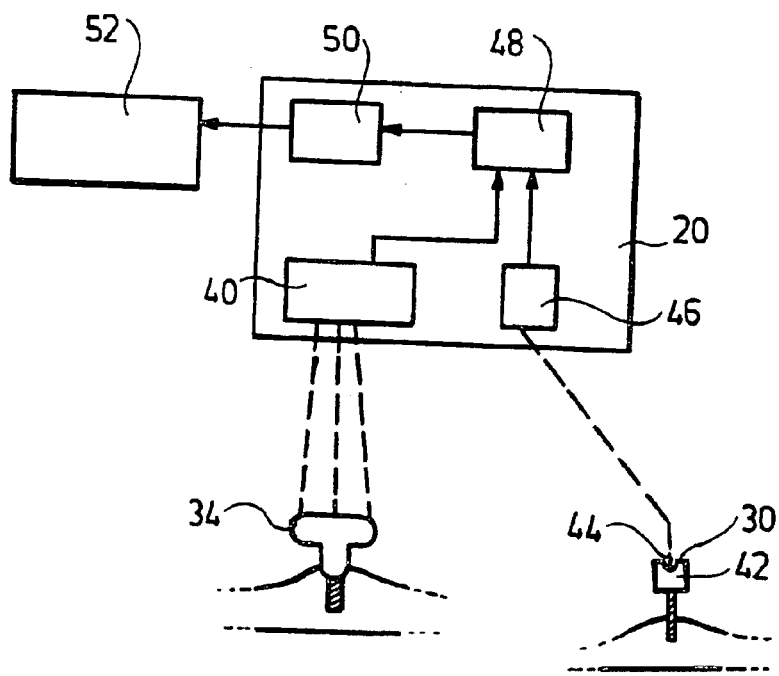

METHOD AND DEVICE FOR CHECKING A MARKING ELEMENT FOR DISPLACEMENT

The present disclosure relates to the subject matter disclosed in German application No. 101 45 587.9 of Sep. 15, 2001, which is incorporated herein by reference in its entirety and for all purposes.

BACKGROUND OF THE INVENTION

The invention relates to a method and a device for checking a marking element for shift or displacement in relation to a holding structure, in particular a bone, on which this marking element is fixed, said marking element being used for determining position in navigational surgery.

In navigational surgery (computer-assisted surgery), robots are used in order, for example, to ream out bone cavities or to make incisions in bone or to saw through bone. By this means, the site of the reaming or the site of the incision can be set with precision. To do so, however, it is necessary that the spatial positions of the machining tools relative to the operating field are known at each point in time with a high degree of accuracy.

For this purpose, marking elements are used which are fixed on a corresponding holding structure or on various holding structures. The marking elements are fixed in particular by using bone screws which are fixed on a corresponding bone. In a hip operation, for example, one or more marking elements are fixed on the corresponding hip bone. When fitting a knee prosthesis, marking elements are fixed on the bones of the foot, on the bones of the lower leg, on the femoral bone, and on the hip bone.

Assuming that the marking elements are fixed securely on the holding structure, a navigation system can be used to determine their spatial position and thus in turn to control the machining tool.

With the present invention, a simple method and a simple apparatus for checking a marking element for displacement in relation to the holding structure is made available, said marking element functioning with the greatest possible precision.

SUMMARY OF THE INVENTION

According to the invention, a method is provided which comprises choosing a point of orientation which is in a unique or clear relationship to the holding structure and in which the position of this point of orientation in a reference system of the marking element is monitored.

The position of the marking element is in any case determined via the navigation, so that the reference system of the marking element, that is to say the rest system of the marking element, is known. By establishing an additional point, namely the point of orientation, which is in a unique and determinable relationship to the holding structure, it is thus possible, by time-resolved and in particular continuous monitoring of the point of orientation for movement in the reference system of the marking element, to detect a displacement of the latter.

If such a displacement is established, then the result of the operation is compromised if the operation is continued without appropriate corrections, because the position indicated by the displaced marking element no longer correlates with the starting position at which the calibration took place. By means of the method according to the invention, a computer-assisted operation can consequently be monitored and, if a displacement is detected, an operator is then informed that a suitable corrective measure is necessary before continuing with the operation, because the position of a marking element has changed.

By means of the procedure according to the invention, namely involving choosing a point of orientation in a unique and clear and determinable relationship to the holding structure, only the movement of this point of orientation has to be detected in order to check for displacement. Since, as has already been mentioned, the position of the marking element is in any case determined continuously by the navigation station, the "positional tracking" of a single point, namely the point of orientation, is accordingly sufficient to carry out a safety check for displacement of each marking element.

Provision can be made for the point of orientation to be in a defined geometric relationship to the holding structure. If, for example, a marking element is fixed as bone screw in a hip bone, and if the patient's upper body and head are fixed relative to a bench, then, for example, any desired point in space represents such a point of orientation.

The point of orientation can also be an anatomical one. In the example described above, the tip of the nose, for example, is one such point of orientation. However, a suitable point of orientation can also be established by a further bone screw with a marker being fixed in the hip bone, a suitable mark on this marker then forming a point of orientation.

Alternatively, or in addition, provision can also be made for the point of orientation to be in a defined kinematic relationship to the holding structure. In the case of a knee, for example, movements of the lower leg relative to the knee, of the upper leg relative to the knee and of the upper leg relative to the hip are in principle possible. However, these movements are not independent of one another and instead are subject to kinematic limitations. A marking element suitably fixed on one of said bones is therefore likewise subject to said kinematic limitations in terms of its movability with the holding structure, which fact can be made use of to construct a "kinematic" point of orientation which is in a unique relationship to the holding structure.

To explicitly establish a point of orientation, provision can be made for this to be chosen by means of a pin element which has a mark whose position is invariable relative to the rotation of the pin element about a pin axis, and which is fixed in a defined relationship to the holding structure. A pin element is less susceptible to displacements than a bone screw. In particular by choosing a mark which is invariable in respect of rotation, it is ensured that a rotation of the pin element is not expressed as a rotation of the mark relative to the holding structure.

It is very particularly advantageous if the marking element comprises a screw for fixing on a bone or is formed by such a screw. Using a bone screw, a marking element can be fixed in a simple and secure manner so that appropriate positional data can be supplied for the navigational surgery.

The marking element and the screw are in this case advantageously calibrated such that the position of a screw axis in the reference system of the marking element is determined. From the relative position between the point of orientation and the reference system of the marking element, it is thus possible to determine the position of the axis and, from the movement of the point of orientation, it is in turn possible to determine its movement relative to the axis. Thus, it is in turn possible to deduce a movement of the marking element relative to the holding structure with respect to its axis, that is to say in particular a displacement along this axis and a rotation about this axis.

In a simple variant of one embodiment, a base vector of the reference system of the marking element is offset parallel to the screw axis. In this way, the calculating work required for converting movements of the point of orientation into displacements of the marking element is kept to a minimum.

In order to check the marking element for displacement, the position of the point of orientation relative to a comparison point of orientation is checked in particular. The comparison point of orientation represents the starting position of the marking element from which checking for displacement is carried out. If the position of the point of orientation relative to the comparison point of orientation changes in the reference system of the marking element, this then means that a corresponding displacement of the marking element relative to the holding structure has taken place.

In particular, the distance between a detected point of orientation and the comparison point of orientation is determined.

Moreover, an orthogonal distance between the detected point of orientation and the marking element is determined. If this orthogonal distance changes, it can be deduced from this that a complicated movement of the marking element has taken place, which movement is probably not to be reproduced, and a corresponding warning signal can then be output as a result so that an operator immediately interrupts the operation.

Provision can further be made to determine a distance between a projection of the comparison point of orientation onto an axis of the marking element and the projection of a detected point of orientation. From this distance, it is possible to deduce a linear displacement of the marking element along this axis.

Provision is further made to determine an angle difference between the detected point of orientation and the comparison point of orientation in a plane perpendicular to an axis of the marking element. From this angle difference, it is possible to determine a rotation of the marking element about its axis and in particular about its screw axis.

In this connection, provision is made in particular for a warning signal to be output if the difference of the orthogonal distance of a detected point of orientation and of a comparison point of orientation is different than zero. A difference different than zero signifies that transverse movements to the axis of the marking element have taken place and that probably the whole movement is not reproducible. The warning signal then indicates to the operator that the position determination in the navigational surgery could be affected by inaccuracies and that for this reason the operation is to be interrupted, so as to be able to recalibrate the navigation.

Provision is further made to indicate a displacement length if the difference of the orthogonal distance of a detected point of orientation and of the orthogonal distance of the comparison point of orientation is determined as zero and the distance of the projections onto an axis of the marking element is different than zero. This distance of the projections then directly indicates the displacement length by which the marking element has moved parallel to its axis. From this, in turn, a navigation station can execute a corresponding calibration in respect of the marking element or, if the computer-assisted operation is accordingly interrupted, the marking element can be reset to its original position, where of course the length of displacement is known.

Provision can further be made to indicate a displacement angle if the difference of the orthogonal distance of a detected point of orientation and the orthogonal distance of a comparison point of orientation is determined as zero and the angle difference in a plane perpendicular to the axis of the marking element between detected point of orientation and comparison point of orientation is different than zero. Such an angle difference then indicates by what angle of rotation (modulo $2\pi$) the marking element has turned about its axis. The marking element can then be turned back accordingly, or the rotation can be taken into account by recalibrating the position of the marking element.

It is a further advantage of the invention that an apparatus of the type mentioned in the introduction for checking a marking element for displacement in relation to the holding structure, said marking element functioning with the greatest possible precision is made available. According to the invention, this is achieved by an apparatus which comprises a navigation device for determining the position of the marking element in space, a device for establishing and/or determining a point of orientation which is in a defined relationship to the holding structure, a device which determines the position of the point of orientation in the reference system of the marking element, and a detection device for checking the marking element for displacement by checking the point of orientation for positional displacement.

The position of the marking element is in any case determined via the navigation, so that the reference system of the marking element, that is to say the rest system of the marking element, is known. By establishing an additional point, namely the point of orientation, which is in a unique and determinable relationship to the holding structure, it is thus possible, by periodical or in particular continuous monitoring of the point of orientation for movement in the reference system of the marking element, to detect a displacement of the latter. If such a displacement is established, then the result of the operation is compromised if said operation is continued without appropriate corrections, because the position indicated by the displaced marking element no longer correlates with the starting position at which the calibration took place. By means of the method according to the invention, a computer-assisted operation can consequently be monitored and, if a displacement is detected, an operator is then informed of the fact that, before continuing the operation, a suitable corrective measure is required because the position of a marking element has moved.

By means of the procedure according to the invention, namely involving choosing a point of orientation in a defined and determinable relationship to the holding structure, only the movement of this point of orientation has to be detected to check for displacement. Since, as has already been mentioned, the position of the marking element is in any case determined continuously by the navigation station, the "positional tracking" of a single point, namely the point of orientation, is accordingly sufficient to carry out a safety check for displacement of each marking element.

The following description of a preferred embodiment serves, together with the drawing, to further explain the invention.

BRIEF DESCRIPTION OF THE DRAWINGS

FIG. 2 shows an example of a movement of a point of orientation in a reference system of a marking element, the distance to the marking element changing;

FIG. 3 shows a further example of a movement of a point of orientation, the distance to the marking element remaining constant, but a projection along the axis of the marking element being displaced;

FIG. 4 shows a further example of a movement of a point of orientation, the distance to the marking element being maintained, but the angle position changing; and FIG. 5 shows a diagrammatic view of a device according to the invention for checking a marking element for displacement.

DETAILED DESCRIPTION OF THE INVENTION

Figure 1:
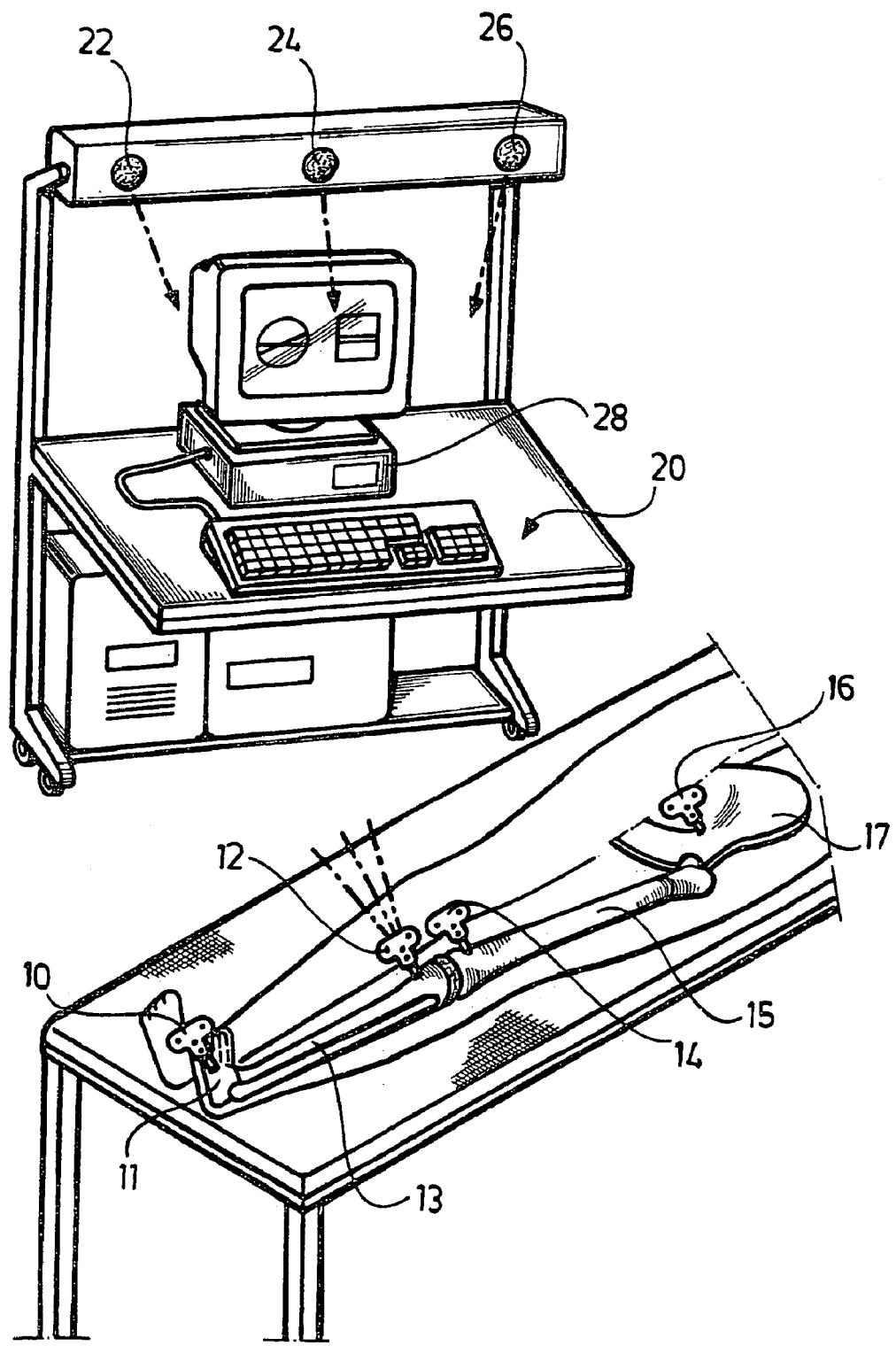
FIG. 1 shows a diagrammatic view of an apparatus by means of which navigational data can be determined in a computer-assisted (navigational) operation.

In computer-assisted surgery (navigational surgery), operating robots are used in order, for example, to ream out bone cavities with a defined arrangement and size or to saw through bone in defined spatial sections. Typical fields of application are operations for implanting endoprostheses. To ensure that the corresponding operating procedures can be executed with a high degree of precision and with the desired result, the spatial position of the machining tool relative to the patient's body must be established; it must in particular be constantly monitored and, if appropriate, corrected.

For positional determination in navigational surgery, marking elements are provided, as are shown for example in FIG. 1. In an operation, for example, one marking element 10 sits on the foot bone 11, one marking element 12 on the bone 13 of the lower leg, one marking element 14 on the femoral bone 15, and one marking element 16 on a hip bone 17.

The bones 11, 13, 15, 17 in each case form a holding structure for the associated marking elements 10, 12, 14, 16.

For fixing it on this holding structure, a marking element comprises a bone screw, so that the marking element can be fixed in a bone. To form the marking element, this bone screw is then provided with a mark via an adapter or the mark is formed directly on the bone screw.

The position of a marking element, for example the marking element 10, in space can be determined via a navigation station 20. For example, a marking element 10 for this purpose comprises a large number of transmitters such as ultrasound transmitters or infrared transmitters whose signals can be registered by receivers 22, 24, 26. In particular, three receivers 22, 24, 26 are provided for the three spatial coordinates.

From the signals received by the receivers 22, 24, 26, the navigation station 20, and in particular a computer unit 28, can then determine the spatial position of the respective marking elements. These positional data can in turn be used, for example, to control a machining tool in navigational surgery.

In principle, it is possible that the positional data of a marking element, for example the marking element 12, determined by the navigation station 20 derive not only from a movement of the holding structure, for example the bone 13 of the lower leg, but also from a movement of the marking element 12 relative to the bone 13 of the lower leg. A bone screw may come loose from the corresponding bone and thus cause a movement of the marking element. So that such a movement is not wrongly interpreted by the navigation station 20, and in particular so that the movement of a marking element relative to its holding structure caused by loosening of the bone screw in relation to the holding structure does not distort the positional data, the invention proposes a method and an apparatus for checking a marking element for displacement in relation to the holding structure.

To this end, as is shown diagrammatically in FIGS. 2 through 4, a point of orientation 30 is chosen which is in a unique and determinable relationship to the holding structure. Depending on the application, this can be an anatomical point, a geometric point or a kinematic point.

In a hip operation, for example, such a point of orientation 30 can be formed by a further bone screw being fixed on the opposite hip bone. Instead of a bone screw, provision can also be made to fix a pin in which, for example, an axial recess is chosen as suitable mark. By choosing an axial recess, a rotation of the pin does not result in a spatial displacement of the point of orientation. If, for example in a hip operation, the patient's upper body is fixed relative to an operating table, then the tip of the nose can also be used as point of orientation.

If it is generally ensured that the holding structure is spatially fixed, then each spatial point can be used as point of orientation.

In a knee operation, a large number of marking elements (compare FIG. 1) are set. The movements of the bones of the lower leg, of the femoral bone at the knee joint, and of the femoral bone relative to the hip, are subject to certain limitations, so that certain conditions for movement possibilities can be derived therefrom. It is in turn possible to establish a kinematic point of orientation which corresponds in a defined and determinable manner with the holding structure, for example the femoral bone 15, on which the marking element 14 is fixed.

According to the invention, the movement of the point of orientation 30 relative to the reference system 32 of a marking element 34 is now determined, so that a shift of the marking element 34 can be deduced from a displacement of the point of orientation 30.

The reference system 32 represents a rest system of the marking element 34, that is to say in this reference system 32 the marking element 34 is at rest. A mark 36 of the marking element is in this case arranged such that the spatial position of an axis 38 of the marking element 34 is known from the position of the mark 36, this axis 38 being in particular an axis of rotation of a bone screw. The marking element 34 with the mark 36 is therefore calibrated such that the position of the axis 38 is known via the spatial position of the mark 36. In particular, the reference system 32 is chosen such that a coordinate axis of this reference system is offset parallel to the axis 38 of the corresponding bone screw.

The navigation station 20 determines the spatial position of the marking element 34 via a navigation means 40, which position is thus known, and thus the reference system 32 can also be established (FIG. 5). A means 46 for establishing and/or determining a point of orientation 30 either establishes the point of orientation or determines the latter, for example via kinematic relationships or as an anatomical point. In FIG. 5, an illustrative embodiment is shown in which the point of orientation 30 is established via a pin element 42 with an axial recess 44 as mark, this pin element then being in a defined relationship to the holding structure of the marking element 34 on which the latter is fixed. The corresponding establishing or determining device 46 can be part of the navigation station 20 or also lie outside of the latter.

A device 48 then determines from these data the position of the point of orientation 30 in the reference system 32 of the marking element 34; this device 48 is thus connected to the navigation device 40 and to the device 46 for establishing the point of orientation 30. The device 48 in turn delivers its data to a detection means 50 which checks the position of the marking element 34 for displacement in relation to the holding structure by means of checking for a movement of the point of orientation 30 in the reference system 32 of the marking element 34.

The result of this check is shown on a display 52. The devices 48, 50 and the display 52 can be part of the navigation station 20 or can be separate from the latter.

A movement of a point of orientation in relation to a comparison point of orientation, which movement has been detected via the detection means 50, is then an indicator of the fact that the marking element 34 has moved in relation to its holding structure and in particular that a bone screw has loosened.

The method according to the invention for checking for shift proceeds as follows:

At the start of the checking procedure, a point of orientation is chosen as comparison point of orientation. This is indicated by reference number 54 in FIGS. 2 through 4. The detection device 50 determines the coordinates of the detected point of orientation 56 resulting from the movement of the point of orientation starting from the comparison point of orientation 54.

The detection device 50 here determines the distance $D_1$ between the detected point of orientation 56 and the comparison point of orientation 54. Moreover, the (orthogonal) distance $D_2$ between the comparison point of orientation 54 and the marking element 34 and the corresponding distance between the detected point of orientation 56 and the marking element 34 are determined, in order thereby to be able to carry out a check for a change in distance.

In addition, the distance $D_3$ on the axis 38 between a projection of the detected point of orientation 56 onto this axis and the projection of the comparison point of orientation 54 onto this axis is also determined.

An angle difference $A_1$ (FIG. 4) in a plane 58 perpendicular to the axis 38 between the detected point of orientation 56 and the comparison point of orientation 54 is determined as a further parameter.

By means of these determined parameters $D_1$, $D_2$, $D_3$ and $A_1$, it is possible, by checking the movement of a single point, namely of the point of orientation 30 in the reference system 32 of the marking element 34, to check the latter for displacement in relation to the holding structure, in which case quantitative conclusions can also be derived from the results.

In the example shown in FIG. 2, in which the comparison point of orientation 54, there indicated by A, migrates toward B, the distance of $D_2^A$ changes to $D_2^B$ ($D_2^A \neq D_2^B$), that is to say the distance of the point of orientation B from the corresponding distance of the comparison point of orientation A changes.

This means that a complicated movement of the marking element 34 relative to its holding structure has taken place, which movement is not reproducible, at least not in a simple manner. A warning signal is thus output on the display 52, so that an operator can tell that a marking element has moved in a nonreproducible manner and a new calibration is needed before the operation can be continued.

An additional check can be carried out by comparing the distances $D_1$ and $D_3$ between the points B and A, respectively, and their projections; if, alternatively or in addition, these are different and the distance $D_3$ is not different than zero, then a warning signal should likewise be output.

In the example shown in FIG. 3, a parallel displacement of the point of orientation 30 occurs: the detected point of orientation is in this case indicated by C, while the comparison point of orientation is once again indicated by A. No change in distance occurs here ($D_2^A = D_2^C$), but the parameter $D_1$ changes, and likewise the parameter $D_3$. A check can additionally be made to see whether the parameters $D_1$ and $D_3$ correspond.

Given identical distances $D_2$, the parameters $D_1$ and $D_3$ are a direct measure of how the marking element has moved along its axis 38, that is to say they can be used to determine the corresponding displacement of the marking element 34 along this axis 38. The movement of the marking element 34 is thereby reproducible.

The detection device 50 can thus directly determine the displacement of the marking element 34 relative to its holding structure. The corresponding value is shown on the display 52 so that an operator, before continuing with the operation, can either bring the marking element 34 back to its previous position or can recalibrate the navigation device 40 according to the reproduced movement of the marking element 34.

In the example shown in FIG. 4, it will be seen that, although the distances $D_2$ ($D_2^A = D_2^E$) are unchanged, an angle change at angle $A_1$ has occurred. The distance change $D_3$ is zero, while the distance change $D_1$ for the detected point of orientation 56 (indicated by E in FIG. 4) is different than zero.

It can thus be deduced that the marking element 34 has turned about the axis 38 without displacement along the latter. The detection means 50 has thus determined the angle of rotation (modulo $2\pi$) via determination of the angle $A_1$, and this value is accordingly shown on the display 52. In this way too, the navigation means 40 can be recalibrated or the marking element 34 can be brought into its starting position so that the point of orientation 30 again lies in its comparison position 54.

There can also be combined rotational movements and linear displacements along the axis 38, corresponding to a combination of the movement examples from FIGS. 3 and 4. If the distance $D_2$ remains unchanged, such a movement is reproducible via the detection means 50, and a corresponding distance $D_3$ and an angle difference $A_1$, which are indicated in particular via the display 52, then show the shift of the marking element 34 relative to the holding structure, provided only that the distances $D_2$ between comparison point of orientation 54 and detected point of orientation 56 remain unchanged.

By means of the apparatus according to the invention and by means of the method according to the invention, a marking element 34 can thus be checked for shift in relation to its holding structure and in particular for displacement along its axis 38 and rotation about its axis 38, and a corresponding displacement can be quantitatively indicated.

In the case of complicated displacements, for example with a direction of displacement at an angle to an axis 38 and/or with angles of rotation with respect to an axis of rotation at an angle to the axis 38 of the marking element 34, a warning signal is output by the apparatus according to the invention, which warning signal informs the operator that the operation must be interrupted on account of problems.

What is claimed is:

1. A method for checking a marking element for displacement in relation to a holding structure, in particular a bone, on which this marking element is fixed, said marking element being used for determining position in navigational surgery, said method comprising:

choosing a point of orientation which is in a unique relationship to the holding structure, and monitoring a position of the point of orientation in a reference system of the marking element.

2. The method of claim 1, wherein the point of orientation is in a unique geometric relationship to the holding structure.

3. The method of claim 1, wherein the point of orientation is an anatomical point of orientation.

4. The method of claim 1, wherein the point of orientation is in a unique kinematic relationship to the holding structure.

5. The method of claim 1, wherein the point of orientation is chosen by means of a pin element which has a mark whose position is invariable relative to rotation of the pin element about a pin axis, and which is fixed in a unique relationship to the holding structure.

6. The method of claim 1, wherein the marking element comprises a screw for fixing on a bone.

7. The method of claim 6, wherein the marking element and the screw are calibrated such that a position of a screw axis in the reference system of the marking element is known.

8. The method of claim 7, wherein a base vector of the reference system of the marking element is offset parallel to the screw axis.

9. The method of claim 1, wherein, in order to check the marking element for displacement, the position of the point of orientation relative to a comparison point of orientation is checked.

10. The method of claim 9, wherein a distance between the detected point of orientation and the comparison point of orientation is determined.

11. The method of claim 9, wherein an orthogonal distance between the detected point of orientation and the marking element is determined.

12. The method of claim 11, wherein a warning signal is output if a difference of an orthogonal distance of the detected point of orientation and of the comparison point of orientation is different than zero.

13. The method of claim 11, wherein a displacement angle is indicated if a difference of the orthogonal distance of the detected point of orientation and of an orthogonal distance of the comparison point is determined as zero and an angle difference in a plane perpendicular to the axis of the marking element between the detected point of orientation and the comparison point of orientation is different than zero.

14. The method of claim 9, wherein a distance between a projection of the detected point of orientation onto an axis of the marking element and a projection of the comparison point of orientation on this axis is determined.

15. The method of claim 12, wherein a displacement length is indicated if a difference of an orthogonal distance of the detected point of orientation and of the comparison point of orientation is determined as zero and the distance of the projections onto an axis of the marking element is different than zero.

16. The method of claim 9, wherein an angle between the detected point of orientation and the comparison point of orientation in a plane perpendicular to an axis of the marking element is determined.

17. An apparatus for checking a marking element for displacement in relation to a holding structure, in particular a bone, on which the marking element is fixed, said marking element being used for determining position in navigational surgery, said device comprising:

a navigation device for determining the position of the marking element in space;

a device for establishing and/or determining a point of orientation which is in a unique relationship to the holding structure;

a device which determines a position of the point of orientation in a reference system of the marking element, and a detection device for checking the marking element for displacement by checking the point of orientation for positional displacement.

18. The apparatus of claim 17, wherein the marking element sits or is formed on a bone screw.

19. The apparatus of claim 18, wherein the marking element and the screw are calibrated such that a position of a screw axis in the reference system of the marking element is known.

20. The apparatus of claim 17, wherein the detection device determines at least one of:

an orthogonal distance between the detected point of orientation and the marking element;

a distance between the detected point of orientation and a comparison point of orientation;

a distance between a projection of the detected point of orientation onto the marking element and a projection of a comparison point of orientation onto the marking element, and an angle difference between the detected point of orientation and a comparison point of orientation in a plane perpendicular to axis of the marking element.

21. The apparatus of claim 17, wherein a pin element is used for setting the point of orientation.

22. The apparatus of claim 21, wherein the pin element has a mark which lies coaxial to a pin axis.

* * * * *

UNITED STATES PATENT AND TRADEMARK OFFICE
CERTIFICATE OF CORRECTION

PATENT NO. : 6,877,239 B2
DATED : April 12, 2005
INVENTOR(S) : Leitner et al.

It is certified that error appears in the above-identified patent and that said Letters Patent is hereby corrected as shown below:

Column 9,
Line 50, change the dependency from "12" to -- 14 --.

Column 10,
Line 49, insert the word -- an -- before the word "axis".

Signed and Sealed this

Twenty-seventh Day of September, 2005

JON W. DUDAS
*Director of the United States Patent and Trademark Office*